US00PP27549P3

(12) United States Plant Patent
Wood

(10) Patent No.: US PP27,549 P3
(45) Date of Patent: Jan. 17, 2017

(54) ***VIBURNUM* PLANT NAMED 'SMNVCDD'**

(50) Latin Name: ***Viburnum nudum* L. var. *cassinoides***
Varietal Denomination: SMNVCDD

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 75 days.

(21) Appl. No.: 14/545,047

(22) Filed: Mar. 19, 2015

(65) Prior Publication Data

US 2016/0278262 P1 Sep. 22, 2016

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Viburnum* plant named 'SMNVCDD', characterized by its compact, upright, mounding and outwardly spreading plant habit; vigorous growth habit; freely branching habit; large inflorescences with numerous white-colored flowers; and good container and garden performance.

2 Drawing Sheets

Botanical designation: *Viburnum nudum* L. var. *cassinoides*.

Cultivar denomination: 'SMNVCDD'.

BACKGROUND OF THE INVENTION

The present invention relates to a new and distinct cultivar of *Viburnum* plant, botanically known as *Viburnum nudum* L. var. *cassinoides* and hereinafter referred to by the name 'SMNVCDD'.

The new *Viburnum* plant is a product of a planned breeding program conducted by the Inventor in Grand Haven, Mich. The objective of the breeding program is to develop new uniform and compact *Viburnum* plants with good container performance.

The new *Viburnum* plant originated from an open-pollination during the spring of 2004 of an unnamed proprietary seedling selection of *Viburnum nudum* L. var. *cassinoides*, not patented, as the female, or seed, parent with an unknown selection of *Viburnum nudum* L. var. *cassinoides* as the male, or pollen, parent. The new *Viburnum* plant was discovered and selected by the Inventor during the spring of 2007 as a single flowering plant from within the progeny of the stated open-pollination in a controlled environment in Grand Haven, Mich.

Asexual reproduction of the new *Viburnum* plant by softwood cuttings in a controlled environment in Grand Haven, Mich. since June, 2007 has shown that the unique features of this new *Viburnum* plant are stable and reproduced true to type in successive generations of asexual reproduction.

SUMMARY OF THE INVENTION

Plants of the new *Viburnum* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNVCDD'. These characteristics in combination distinguish 'SMNVCDD' as a new and distinct *Viburnum* plant:

1. Compact, upright, mounding and outwardly spreading plant habit.
2. Vigorous growth habit.
3. Freely branching habit.
4. Large inflorescences with numerous white-colored flowers.
5. Good container and garden performance.

Plants of the new *Viburnum* can be compared to plants of the female parent selection. Plants of the new *Viburnum* differ primarily from plants of the female parent selection in plant habit as plants of the new *Viburnum* are more compact than plants of the female parent selection.

Plants of the new *Viburnum* can be compared to plants of the *Viburnum nudum* L. var. *cassinoides* 'Bulk', not patented. Plants of the new *Viburnum* differ from plants of 'Bulk' in the following characteristics:

1. Plants of the new *Viburnum* are more compact than plants of 'Bulk'.
2. Leaves of plants of the new *Viburnum* are brighter green in color than leaves of plants of 'Bulk'.

BRIEF DESCRIPTION OF THE PHOTOGRAPHS

The accompanying colored photographs illustrate the overall appearance of the new *Viburnum* plant showing the colors as true as it is reasonably possible to obtain in colored reproductions of this type. Colors in the photographs may differ slightly from the color values cited in the detailed botanical description which accurately describe the colors of the new *Viburnum* plant.

The photograph on the first sheet is a side perspective view of a typical flowering plant of 'SMNVCDD' grown in a container.

The photograph on the second sheet is a close-up view of a typical flowering plant of 'SMNVCDD' grown in a ground bed.

DETAILED BOTANICAL DESCRIPTION

The aforementioned photographs and following observations, measurements and values describe plants of the new *Viburnum* grown in three-gallon containers during the late spring in a polypropylene-covered shadehouse in Grand Haven, Mich. and under cultural practices typical of commercial *Viburnum* production. During the production of the plants, day temperatures ranged from 18° C. to 27° C. and night temperatures ranged from ranged from 5° C. to 10° C. Plants were two years old when the photographs and the description were taken. In the description, color references are made to The Royal Horticultural Society Colour Chart, 1995 Edition, except where general terms of ordinary dictionary significance are used.

Botanical classification: *Viburnum nudum* L. var. *cassinoides* 'SMNVCDD'.

Parentage:

*Female, or seed, parent*.—Unnamed proprietary seedling selection of *Viburnum nudum* L. var. *cassinoides*, not patented.

*Male, or pollen, parent*.—Unknown selection of *Viburnum nudum* L. var. *cassinoides*, not patented.

Propagation:

*Type*.—By softwood cuttings.

*Time to initiate roots, summer*.—About 20 days at temperatures about 27° C.

*Time to produce a rooted young plant, summer*.—About three months at temperatures about 27° C.

*Root description*.—Fine to thick; white and brown in color.

*Rooting habit*.—Freely branching; dense.

Plant description:

*Plant and growth habit*.—Perennial shrub; compact, upright, mounding and outwardly spreading plant habit; vigorous growth habit.

*Branching habit*.—Freely branching habit with about 14 lateral branches developing per plant; pinching (removal of terminal apices) will enhance lateral branch development.

*Plant height*.—About 39 cm.

*Plant diameter* (*area of spread*).—About 58 cm.

Lateral branch description:

*Length*.—About 34 cm.

*Diameter*.—About 7 mm.

*Internode length*.—About 6 cm.

*Texture*.—Smooth, glabrous.

*Strength*.—Strong.

*Aspect*.—Erect to about 45° from vertical.

*Color*.—Close to 143C; with development, closer to 147B.

Leaf description:

*Arrangement*.—Opposite, simple.

*Length*.—About 7.5 cm.

*Width*.—About 3.6 cm.

*Shape*.—Ovate to lanceolate.

*Apex*.—Acuminate.

*Base*.—Attenuate to oblique.

*Margin*.—Serrulate.

*Texture, upper surface*.—Smooth, glabrous.

*Texture, lower surface*.—Slightly pubescent.

*Venation pattern*.—Pinnate.

*Color*.—Developing leaves, upper surface: Close to 146C; towards the margins, close to 165B. Developing leaves, lower surface: Close to 146D. Fully expanded leaves, upper surface: Close to 137A; venation, close to 145A. Fully expanded leaves, lower surface: Close to 137C; venation, close to 145B.

*Petioles*.—Length: About 1.8 cm. Diameter: About 2 mm. Texture, upper and lower surfaces: Slightly pubescent. Color, upper and lower surfaces: Close to 146C.

Flower description:

*Flower appearance and arrangement*.—Single rotate flowers arranged in terminal cymes; freely flowering habit with usually more than 500 flowers per inflorescence; flowers face upright to outwardly.

*Natural flowering season*.—Flowering commences in late spring to early summer in Michigan; flowers not persistent.

*Fragrance*.—Slightly fragrant; sweet, honey-like.

*Inflorescence height*.—About 7.5 cm.

*Inflorescence diameter*.—About 10.3 cm.

*Flower diameter*.—About 4 mm to 5 mm.

*Flower length* (*height*).—About 4 mm.

*Flower buds*.—Length: About 1.5 mm. Diameter: About 1.5 mm. Shape: Globose. Color: Close to 143C; with development, closer to 155B.

*Petals*.—Quantity per flower: Five petals in a single whorl; fused at the base. Length: About 2 mm. Width: About 1 mm. Shape: Oblong. Apex: Obtuse. Margin: Entire. Texture, upper and lower surfaces: Smooth, glabrous. Color: When opening, upper and lower surfaces: Close to 49C. Fully opened, upper and lower surfaces: Close to 155D.

*Sepals*.—Quantity per flower: Five sepals in a single whorl; fused at the base. Length: Less than 1 mm. Width: Less than 1 mm. Shape: Oblong. Apex: Acute. Margin: Entire. Texture, upper and lower surfaces: Smooth, glabrous. Color: When opening, upper and lower surfaces: Close to 146D. Fully opened, upper and lower surfaces: Close to 146D.

*Peduncles*.—Length: About 6 mm. Diameter: About 1 mm. Strength: Strong. Aspect: Upright to outwardly. Texture: Smooth, glabrous. Color: Close to 200C.

*Pedicels*.—Length: About 1 mm. Diameter: Less than 1 mm. Strength: Strong. Aspect: Upright to outwardly. Texture: Smooth, glabrous. Color: Close to 144C.

*Reproductive organs*.—Androecium: Quantity per flower: About five. Anther shape: Oblong. Anther length: Less than 1 mm. Anther color: Close to 8A and 50C. Amount of pollen: Scarce. Pollen color: Close to 8A. Gynoecium: Quantity per flower: One. Pistil length: Less than 1 mm. Style length: Less than 1 mm. Style color: Close to 144C. Stigma shape: Rounded, three-lobed. Stigma color: Close to 144C. Ovary color: Close to 144C. Fruits and seeds: Fruit and seed development has not been observed on plants of the new *Viburnum*.

Garden performance: Plants of the new *Viburnum* have been observed to have good garden and container performance and to tolerate rain, wind and temperatures ranging from about −27° C. to about 38° C.

Pathogen & pest resistance: Plants of the new *Viburnum* have not been observed to be resistant to pathogens and pests common to *Viburnum* plants.

It is claimed:

1. A new and distinct *Viburnum* plant named 'SMN-VCDD' as illustrated and described.

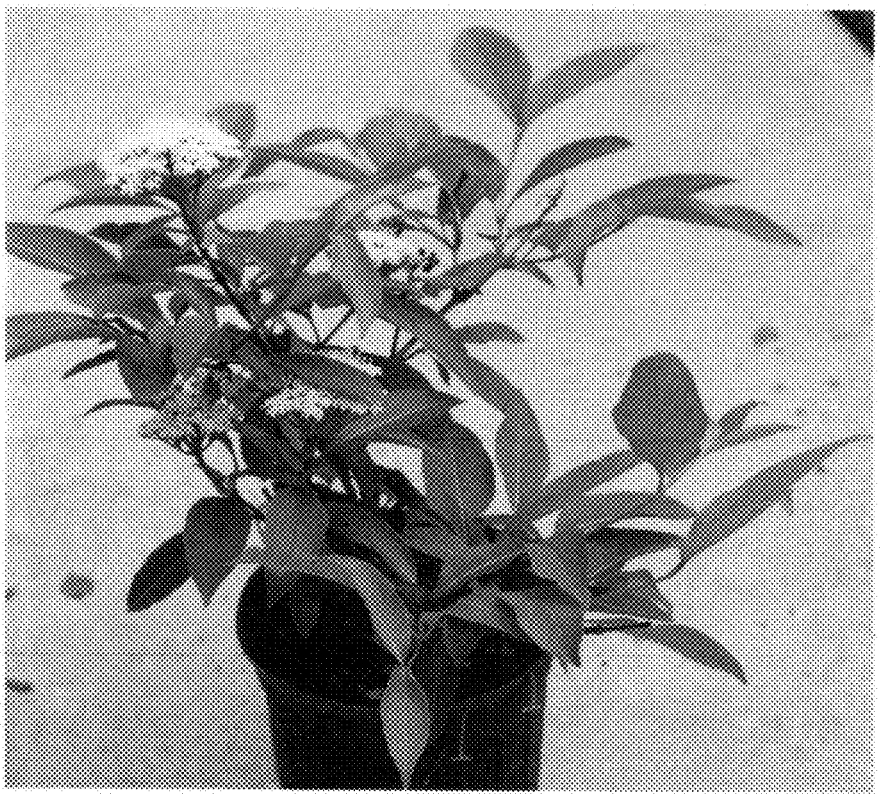

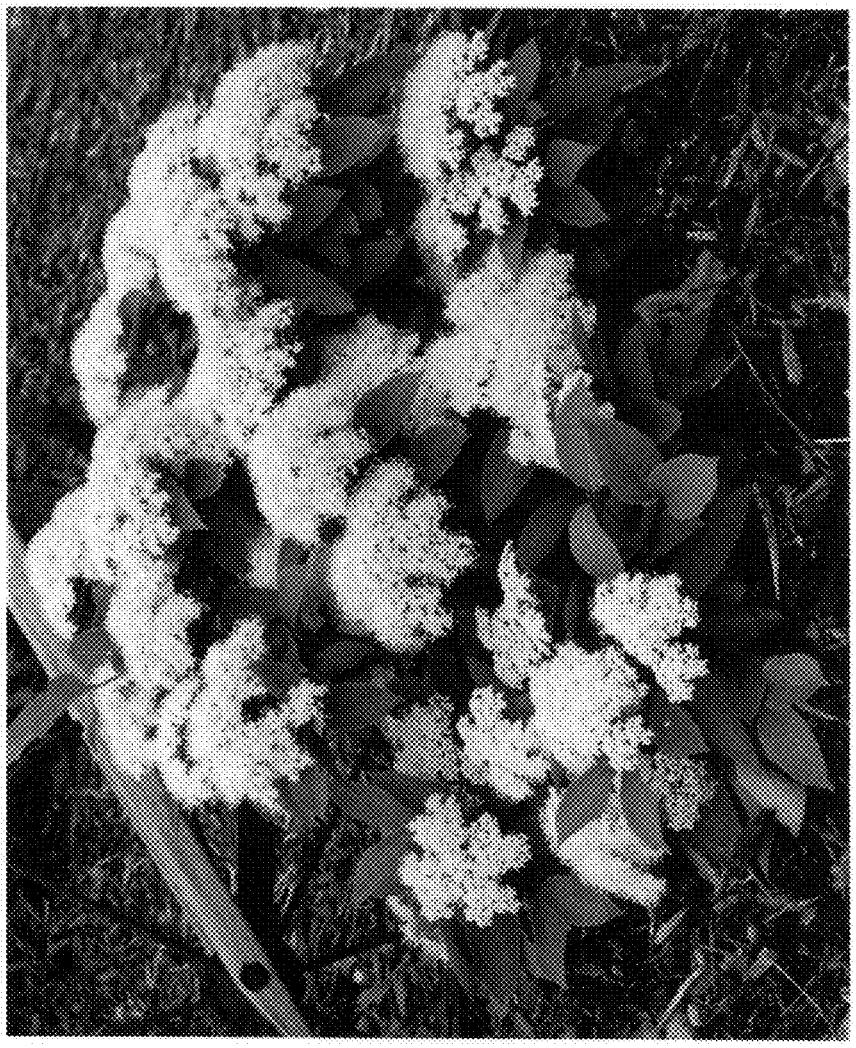

* * * * *